US00PP21429P2

(12) United States Plant Patent
Kordes

(10) Patent No.: US PP21,429 P2
(45) Date of Patent: Nov. 2, 2010

(54) SHRUB ROSE PLANT NAMED 'KORBASPRO'

(50) Latin Name: *Rosa hybrida*
Varietal Denomination: KORbaspro

(75) Inventor: Tim-Hermann Kordes, Klein Offenseth-Sparrieshoop (DE)

(73) Assignee: W. Kordes' Söhne Rosenschulen GmbH & Co KG, Offenseth-Sparrieshoop (DE)

( * ) Notice: Subject to any disclaimer, the term of this patent is extended or adjusted under 35 U.S.C. 154(b) by 0 days.

(21) Appl. No.: 12/459,164

(22) Filed: Jun. 25, 2009

(51) Int. Cl.
*A01H 5/00* (2006.01)

(52) U.S. Cl. ..... Plt./107
(58) Field of Classification Search ..... Plt./107
See application file for complete search history.

(56) References Cited

OTHER PUBLICATIONS

2008/1244, European Union CVPO summary, Aug. 15, 2008, European Union.

*Primary Examiner*—Susan B McCormick Ewoldt

(57) ABSTRACT

A new and distinct variety of rose with long lasting, novel soft pink flowers, and attractive foliage with good disease resistance. It exhibits uniform, upright to bushy growth with abundant flowers. The new variety propagates well from cuttings and by grafting. This new and distinct variety has shown to be uniform and stable in the resulting generations from asexual propagation.

1 Drawing Sheet

CROSS REFERENCES AND FEDERAL R&D STATEMENT

There are no cross-referenced or related applications. This variety was developed without the aid of any research grant.

SUMMARY OF THE INVENTION

Genus, species and variety denomination: The botanical classification of the new rose plant is *Rosa hybrida,* 'KORbaspro'.

BACKGROUND OF THE INVENTION

The new variety of rose plant of the present invention originated from a controlled crossing in a breeding program of two distinct parents during the summer of 1998. The crossing was between 'KORmixal' and 'KORparesni', both non-patented roses.

The resulting seeds were planted during the following winter. The resulting seedlings were evaluated and exhibited distinctive physical and biological characteristics. The new rose plant was selected as a single plant from the seedling beds due to its superior characteristics and asexually propagated for further evaluation. This new and distinctive rose variety is named 'KORbaspro'.

SUMMARY OF THE INVENTION

The new rose plant may be distinguished from its seed parent, 'KORmixal' by the following combination of characteristics:

1. The flower color of the seed parent is red, while the flower color of 'KORbaspro' is pink.
2. The petal count of the seed parent is single, while the petal count of 'KORbaspro' is very double.

The new rose plant may be distinguished from its pollen parent, 'KORparesni' by the following combination of characteristics:

1. The growth habit of the pollen parent is upright, while the growth habit of 'KORbaspro' is spreading.

2. The petal count of the pollen parent is semi-double, while the petal count of 'KORbaspro' is very double.

The objective of the hybridization was to create a new and distinct rose plant with unique qualities, such as:

1. Uniform growth and flowering;
2. Abundant attractive, recurrent flowers;
3. Attractive and abundant foliage; and
4. Resistance to diseases encountered in landscapes and gardens.

This combination of qualities is not present in prior rose cultivars known to the inventor. These objectives have been substantially achieved and in that distinguish 'KORbaspro' from all other varieties of which we are aware.

As part of a rose development program, Tim-Hermann Kordes germinated seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORbaspro' was selected in May, 1998 from the seedling beds to be asexually propagated for further evaluation. The first asexual propagation of 'KORbaspro' was done by budding to seedling understocks in August, 1998 at the inventor's nursery in Offenseth-Sparrieshoop, Germany.

This initial and other subsequent propagations conducted in controlled environments demonstrate that 'KORbaspro' reproduces true to type in successive generations of asexual reproduction.

BRIEF DESCRIPTION OF THE DRAWING

The accompanying drawing shows as true as is reasonably possible to obtain in color photographs of this type, the typical characteristics of the buds, flowers, reproductive organs, leaves, and stems of 'KORbaspro'.

DETAILED BOTANICAL DESCRIPTION

The following is a description of 'KORbaspro', as observed growing in October, 2008 in a nursery in Jackson County, Oreg. on plants of two years of age. Color references are made using The Royal Horticultural Society (London, England) Colour Chart, 2001 except where common terms of color are used.

For a comparison, several physical characteristics of the rose variety 'KORfloci04', a rose variety from the same inventor described and illustrated in U.S. Plant Pat. No.19,457 and issued on Nov. 18, 2008 are compared to 'KORbaspro' in Chart 1.

CHART 1

| Characteristic | 'KORbaspro' | 'KORfloci04' |
|---|---|---|
| Flower bud color (¼ open) upper surface | Red Group 56D | Red Group 56C |
| Open flower diameter | 60-65 mm | 70-75 mm |
| Incidence of thorns per 10 cm of stem | 12-16 | 20-25 |

Parents:

*Seed parent.*—'KORmixal'.

*Pollen parent.*—'KORparesni'.

Classification:

*Botanical classification.*—*Rosa hybrida,* 'KORbaspro'.

*Commercial classification.*—Shrub.

FLOWER AND FLOWER BUD

*Blooming habit.*—Continuous.

*Flower bud.*—Size: Upon opening, 15-17 mm in length from base of receptacle to end of bud and 20-25 mm diameter at its widest point. Bud form: Globular. Bud color: As sepals first unfold, bud color is Red Group 56B and Red Group 56C. When ¼ open, the upper surface of petals is Red Group 56D and the lower surface is Red Group 56D. Guard Petals Yellow-Green Group 145B. Sepals: Size: Average 20 mm long×10 mm wide. Shape: Sepals generally subulate. Sepal apex is generally cirrose. Weak foliaceous appendages on three of the five sepals. Base is flat at union with receptacle. Quantity: Five. Margins: With stipitate glands. Surface texture: Inner side: Covered in small white hairs. Outer surface: Smooth. Stipitate glands are absent. Color: Upper surface Yellow-Green Group 146A. Lower surface Yellow-Green Group 146B.

*Receptacle.*—Surface: Smooth. Color: Yellow-Green Group 144A. Shape: Funnel-shaped. Size: 9-10 mm (h)×9-10 mm (w).

*Peduncle.*—Surface: With stipitate glands. Length: 30-35 mm average length. Diameter: 2.0 mm average diameter. Color: Yellow-Green Group 144B. Strength: Moderate. Borne: Multiple buds per stem. Generally, 5-8 buds per flowering stem. Anthocyanin: Greyed-Purple Group 184A.

Flower bloom:

*Fragrance.*—None.

*Duration.*—On the plant 5-6 days. Long lasting. Senesced petals drop away cleanly.

*Size.*—Medium flowered garden rose. When open, the average flower diameter is 55-65 mm and the average flower height is 30 mm.

*Form.*—Shape of flower when viewed from the side: Upon opening, upper part: Flattened convex. Upon opening, lower part: Flattened convex. Open flower, upper part: Flat. Open flower, lower part: Concave.

Color:

*Upon opening, petals.*—Outermost petals: Outer Side: Red Group 56D. Inner Side: Red Group 56D. Innermost petals: Outer Side: Red Group 56D. Inner Side: Red Group 56D.

*Upon opening, basal petal spots.*—Basal petal spot, outermost petals: Outer Side: Green-Yellow Group 1D. Inner Side: Green-Yellow Group 1D. Basal petal spot, innermost petals: Outer Side: Green-Yellow Group 1D. Inner Side: Green-Yellow Group 1D.

*After opening, petals.*—Outermost petals: Outer Side: White Group N155B. Inner Side: White Group N155B. Innermost petals: Outer Side: White Group N155B. Inner Side: Red Group 56D.

*After opening, basal petal spots.*—Basal petal spot, outermost petals: Outer Side: Green-Yellow Group 1D. Inner Side: Green-Yellow Group 1D. Basal petal spot, innermost petals: Outer Side: Green-Yellow Group 1D. Inner Side: Green-Yellow Group 1D.

General Tonality: On open flower Red Group 56D. No change in the general tonality at the end of the $5^{th}$ day. Afterwards, general tonality is White Group N155B.

Petals:

*Petal count.*—Approximately 70-80 petals under normal conditions.

*Petal reflex.*—Petals reflex somewhat.

*Petal edge.*—Entire with slight point in center of margin.

*Petal shape.*—Apex shape is round. Shape of base is acute.

*Petal size.*—25 mm long; 20-22 mm wide.

*Thickness.*—Thin.

*Flower shape/arrangement.*—Quartered rosette. Generally in a regular pattern with overlapping edges.

Petaloids: Present.

*Petaloid count.*—Average of 2-5 per flower.

*Petaloid edge.*—Smooth.

*Petaloid texture.*—Smooth.

*Petaloid shape.*—Linear to elliptic. Shape of base is acute. Shape of apex is a rounded point.

*Petaloid size.*—Petaloids are 15 mm long and 6 mm wide.

*Petaloid color.*—Color of inner side is Red Group 56C. Color of outer side is Red Group 56D.

Reproductive organs:

*Pistils.*—Approximately 50 present. Stigmas: Location: Slightly superior in position to anthers. Color: Greyed-Yellow Group 160C. Styles: Length: 6-7 mm long. Color: Green-Yellow Group 145C.

*Stamens.*—Approximately 5-10 on average and regularly arranged. Anthers: Size: 2-3 mm long. Color: Yellow-Orange Group 16A. Pollen: Absent. Filaments: Color: Yellow Group 13B. Length: 5-6 mm.

THE PLANT

*Plant growth.*—Vigorous. Upright to bushy habit. When grown as a budded plant the average plant height is 75-85 cm and the average plant width is 50-60 cm.

*Stems.*—Stem color: Young wood: Yellow-Green Group 145A. Older Wood: Green Group 137B. Stem surface: Young wood: Smooth. Older wood: Smooth.

*Prickles.*—Present. Incidence: 12-16 per 10 cm of stem. Size: Average length: 8-9 mm. Color: Immature prickles: Greyed-Yellow Group 162B. Mature prickles: Greyed-Orange Group 164A. Senescing to Greyed-Orange Group 166B. Shape: Deeply concave to concave. Anthocyanin: Color: Greyed-Purple Group 184A.

*Leaves and leaflets.*—Normally 5-7 leaflets on normal leaves in middle of the stem. Leaf size: 110 mm (1)× 70 mm (w). Quantity: Average. Texture: Upper side of leaflet: Semi-glossy. Smooth. Under side of leaflet: Matte. Smooth. Color, mature foliage: Upper Leaf Surface: Green Group 137A. Lower Leaf Surface: Yellow-Green Group 146B. Color, juvenile foliage: Upper Leaf Surface: Green Group 137A. Lower Leaf Surface: Yellow-Green Group 146B. Anthocyanin intonation: Absent.

*Stipules.*—Size: 20-22 mm long. 10 mm between the tips of the stipule. Main body of stipule 6-9 mm in width. Shape: Longitudinally flanged or winged along middle. Winged tips turn downwards. Stipule color: Green Group 138A. Anthocyanin: Greyed-Purple Group 184B. Presence of stipitate glands: Present on margins. Margins: With stipitate glands.

*Petiole.*—Length: 10-15 mm. Diameter: 1.0-1.5 mm. Petiole color: Yellow-Green Group 144A. Anthocyanin present on juvenile tissue, Greyed-Purple Group 184A. Underneath: Smooth. Stipitate glands: Absent.

*Petiole rachis.*—Length: 15-20 mm. Diameter: 1.0-1.5 mm. Color: Yellow-Green Group 144A. Anthocyanin present on juvenile tissue, Greyed-Purple Group 184A. Margins: Stipitate glands present. Prickles: Occasional. Stipitate glands: Present on margins.

*Leaflets.*—Size: Average size of the terminal leaflet is 45 mm (1)×25-30 mm (w). Shape: Ovate. Base: Ovate. Apex: Acute. Margins: Serrated. Texture: Thin. Moderately glossy.

Hips/seed formation: Absent.

Winter hardiness: To date, the variety has been grown successfully in Zone 5.

Disease resistance: Above average resistance to Powdery mildew (*Sphaerotheca pannosa*), rust (*P. disciflorum*), blackspot (*Diplocarpon rosae*), and Botrytis (*Botrytis cinerea*) diseases under normal growing conditions.

I claim:

1. A new and distinct variety of rose plant as herein illustrated and described:

(a) Forms attractive, long lasting soft pink flowers;

(b) Exhibits uniform, upright to bushy growth habit;

(c) Propagates well using traditional methods, and;

(d) Exhibits very good resistance to disease under normal growing conditions, substantially as herein illustrated and described.

* * * * *

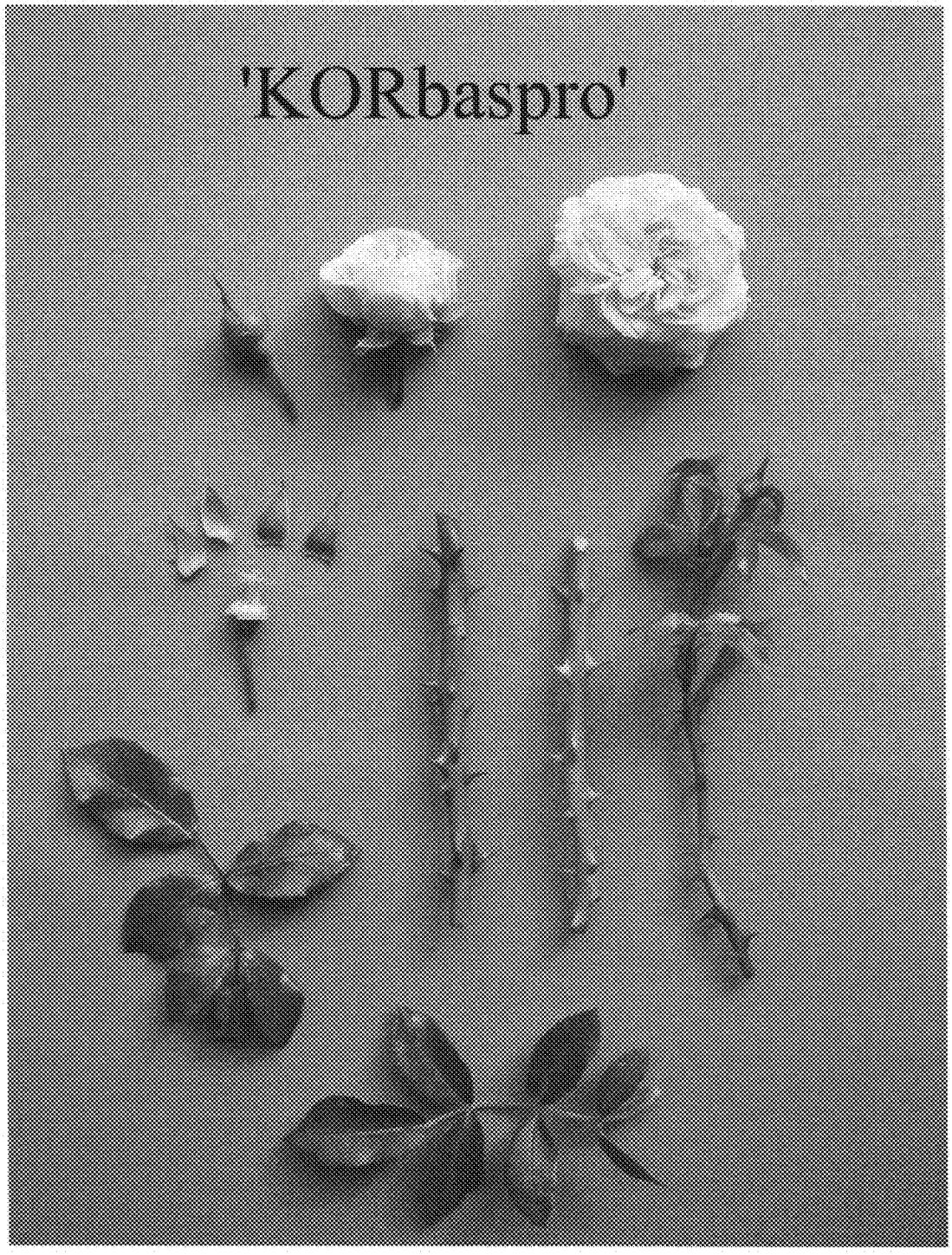
'KORbaspro'